(12) United States Patent
Duffy et al.

(10) Patent No.: US 6,552,008 B1
(45) Date of Patent: Apr. 22, 2003

(54) THROMBOPOIETIN MIMETICS

(75) Inventors: Kevin J. Duffy, Norristown, PA (US); Nannan Liu, Audubon, PA (US); Juan I. Luengo, Audubon, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/110,287

(22) PCT Filed: Sep. 22, 2000

(86) PCT No.: PCT/US00/26059

§ 371 (c)(1), (2), (4) Date: Mar. 22, 2002

(87) PCT Pub. No.: WO01/21180

PCT Pub. Date: Mar. 29, 2001

Related U.S. Application Data

(60) Provisional application No. 60/155,958, filed on Sep. 24, 1999.

(51) Int. Cl.$^7$ .................... A61K 31/655; C07D 403/12
(52) U.S. Cl. ........................... 514/150; 534/769
(58) Field of Search ........................... 514/150; 534/769

(56) References Cited

U.S. PATENT DOCUMENTS 2,950,273 A    8/1960  Pelz et al. .................. 534/587

OTHER PUBLICATIONS

Database Caplus on STN, Chemical Abstracts Service (Columbus, OH, USA) No. 95:152136, Balli et al., "Tautomerism of o,o'–diamino– and o,o'–dihydroxyazopyrazole Dyes", abstract, 1981.
Database Caplus on STN, Chemical Abstracts Service (Columbus, OH, USA) No. 66:47281, Balli et al., "Azidinium Salts. V. Symmetric azo–5–pyrazolone dyes by azo group transition of heterocyclic azidinium salts to 1–(X–substituted phenyl)–3–methyl–5–pyrazolones", abstract, 1967.
Dziomko, et al., Chem. Heterocycl. Compd, 1984, vol. 20, No. 2, pp. 196–200. XP001096480.

*Primary Examiner*—Fiona T. Powers
(74) *Attorney, Agent, or Firm*—Wayne J. Dustman; Stephen Venetianer; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a selected azopyrazole derivative.

14 Claims, No Drawings

THROMBOPOIETIN MIMETICS

This is a 371 of International Application PCT/US00126059, filed Sep. 22, 2000, which claims benefit from the following Provisional Application: 60/155,598, filed Sep. 24, 1999.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter et al. *Proc. Natl. Acad. Aci. USA* 91: 11104–11108 (1994). Megakaryocytes undergo a process known as endomitosis whereby they replicate their nuclei but fail to undergo cell division and thereby give rise to polypoid cells. In response to a decreased platelet count, the endomitotic rate increases, higher ploidy megakaryocytes are formed, and the number of megakaryocytes may increase up to 3-fold. See Harker *J. Clin. Invest.* 47: 458–465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitrotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519–520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See e.g., McDonald (1992) *Am. J. Ped. Hematology/Oncology* 14: 8–21 (1992).

The gene encoding TPO has been cloned and characterized. See Kuter et al., *Proc. Natl. Acad. Sci. USA* 91: 11104–11108 (1994); Barley et al., *Cell* 77: 1117–1124 (1994); Kaushansky et al., *Nature* 369:568–571 (1994); Wendling et al., *Nature* 369: 571–574 (1994); and Sauvage et al., *Nature* 369: 533–538 (1994). Thrombopoietin is a glycoprotein with at least two forms, with apparent molecular masses of 25 kDa and 31 kDa, with a common N-terminal amino acid sequence. See, Bartley, et al., *Cell* 77: 1117–1124 (1994). Thrombopoietin appears to have two distinct regions separated by a potential Arg-Arg cleavage site. The amino-termninal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. See, Vigon et al. *Proc. Natl. Acad. Sci. USA* 89: 5640–5644 (1992). TPO-R is a member of the haematopoletin growth factor receptor family, a family characterized by a common structural design of the extracellular domain, including for conserved C residues in the N-terminal portion and a WSXWS motif close to the transmembrane region. See Bazan *Proc. Natl. Acad. Sci. USA* 87: 6934–6938 (1990). Evidence that this receptor plays a functional role in hematopoiesis includes observations that its expression if restricted to spleen, bone marrow, or fetal liver in mice (see Souyri et al. *Cell* 63: 1137–1147 (1990)) and to megakaryocytes, platelets, and CD34$^+$ cells in humans (see Methia et al. *Blood* 82: 1395–1401 (1993)). Further evidence for TPO-R as a key regulator of megakaryopoiesis is the fact that exposure of CD34$^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The slow recovery of platelet levels in patients suffering from thrombocytopenia is a serious problem, and has lent urgency to the search for a blood growth factor agonist able to accelerate platelet regeneration.

It would be desirable to provide compounds which allow for the treatment of thrombocytopenia by acting as a TPO mimetic.

As disclosed herein it has unexpectedly been discovered that certain azo-pyrazole derivatives are effective as agonists of the TPO receptor, they are potent TPO mimetics.

SUMMARY OF THE INVENTION

This invention relates to compounds of Formula (I):

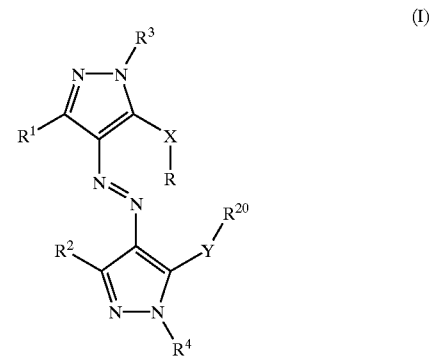

wherein:
X and Y are independently selected from sulfur, oxygen, an amino group which is optionally substituted by $C_1$–$C_{10}$alkyl, benzyl or phenyl;

R and $R^{20}$ is selected from hydrogen, alkyl, cycloalkyl, $C_1$–$C_{12}$aryl, substituted alkyl, substituted cycloalkyl and substituted $C_1$–$C_{12}$aryl;

$R^1$ and $R^2$ are each independently selected from hydrogen, alkyl, cycloalkyl, aryl, substituted alkyl, substituted cycloalkyl, substituted aryl, alkoxy, substituted alkoxy, —(CH$_2$)$_m$OR$^5$, sulfonic acid, —COOR$^5$, nitro, amino, —NR$^6$R$^7$, N-acylamino, —N(R$^{10}$)C(O) R$^{11}$, —N(R$^{10}$)C(O)NR$^6$R$^7$, —N(R$^{10}$)SO$_2$R$^{11}$, cyano, halogen, —S(O)$_n$R$^5$, protected —OH, —CONR$^6$R$^7$, phosphonic acid, phosphinic acid and —SO$_2$NR$^6$R$^7$, where m is 0–6;

$R^5$ is selected from hydrogen, alkyl, cycloalkyl, $C_1$–$C_{12}$aryl, substituted alkyl, substituted cycloalkyl and substituted $C_1$–$C_{12}$aryl, $R^6$ and $R^7$ are each independently selected from hydrogen, alkyl, $C_{3-6}$cycloalkyl, phenyl, $C_1$–$C_{12}$aryl or $R^6$ and $R^7$ taken together with the nitrogen to which they are attached represent a 5 to 6 member saturated ring containing up to one other heteroatom selected from oxygen and nitrogen, $R^{10}$ and $R^{11}$ are each independently selected from hydrogen, alkyl, $C_{3-6}$cycloalkyl, $C_1$–$C_{12}$aryl and n is 0–2;

$R^3$ and $R^4$ are independently selected from alkyl, cycloalkyl, substituted alkyl, substituted cycloalkyl, —(CH$_2$)$_m$COOR$^5$ and a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, $C_1$–$C_{12}$aryl, substituted cycloalkyl, substituted $C_1$–$C_{12}$aryl, aryloxy, hydroxy, alkoxy, cycloalkyl, acyloxy, amino, N-acylamino, nitro, cyano, halogen, —C(O)OR$^{12}$, —C(O)NR$^8$R$^9$, —S(O)$_2$NR$^8$R$^9$, —S(O)$_n$R$^5$, protected —OH and alkyl substituted with one or more substituents selected from the group consisting of: alkoxy, acyloxy, $C_1$–$C_{12}$aryl, substituted $C_1$–$C_{12}$aryl, amino, N-acylamino, oxo, hydroxy, cycloalkyl, substituted cycloalkyl, —C(O)OR$^{12}$, —S(O)$_2$NR$^8$R$^9$, —S(O)$_n$R$^5$, aryloxy, nitro, cyano, halogen, and protected —OH, where m is 0–6, $R^5$ is selected from hydrogen, alkyl, cycloalkyl, $C_1$–$C_{12}$aryl, substituted alkyl, substituted cycloalkyl and substituted $C_1$–$C_{12}$aryl, $R^8$ and $R^9$ are independently selected form hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —C(O)OR$^5$, —S(O)$_n$R$^5$, C(O)NR$^5$R$^5$, S(O)$_2$NR$^5$R$^5$, nitro, cyano, cycloalkyl, substituted cycloalkyl, halogen, $C_1$–$C_{12}$aryl, substituted $C_1$–$C_{12}$aryl and protected —OH where R$^5$ and n are as described above, or R$^8$ and R$^9$ taken together with the nitrogen to which they are attached represent a 5 to 6 member saturated ring containing up to one other heteroatom selected from oxygen and nitrogen, $R^{12}$ is selected form hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —C(O)OR$^5$, —S(O)$_n$R$^5$, C(O)NR$^5$R$^5$, S(O)$_2$NR$^5$R$^5$, nitro, cyano, cycloalkyl, substituted cycloalkyl, halogen, $C_1$–$C_{12}$aryl, substituted $C_1$–$C_{12}$aryl and protected —OH where R$^5$ and n are as described above, and n is 0–2; and pharmaceutically acceptable salts, hydrates, solvates and esters thereof.

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

The presently invented compounds that act as TPO mimetics are defined by Formula (I) above.

Preferred among the presently invented Formula I compounds are those in which R and $R^{20}$ are hydrogen; X and Y are independently selected from sulfur, oxygen, an amino group which is optionally substituted by $C_1$–$C_{10}$alkyl, benzyl or phenyl; $R^1$ and $R^2$ are each independently selected from hydrogen, carboxylic acid, $C_{1-6}$alkoxy, nitro, $C_{1-6}$alkyl, $C_{6-12}$aryl and haloaen; and $R^3$ and $R^4$ are each independently selected from a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, carboxylic acid, sulfonic acid, substituted alkyl, $C_6$–$C_{12}$aryl, substituted cycloalkyl, substituted $C_6$–$C_{12}$aryl, aryloxy, hydroxy, alkoxy, cycloalkyl, amino, nitro, cyano, halogen and protected —OH; and pharmaceutically acceptable salts, hydrates, solvates and esters thereof.

Particularly preferred among the presently invented Formula I compounds are those in which R and $R^{20}$ are hydrogen; X and Y are independently selected from sulfur, oxygen, an amino group which is optionally substituted by $C_1$–$C_{10}$alkyl, benzyl or phenyl; $R^1$ and $R^2$ are each independently selected from carboxylic acid, $C_{1-6}$alkoxy, $C_{1-6}$alkyl and phenyl; and $R^3$ and $R^4$ are each independently selected from a cyclic or polycyclic aromatic ring containing from 3 to 14 carbon atoms and optionally containing from one to three heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, carboxylic acid, sulfonic acid, substituted alkyl, $C_6$–$C_{12}$aryl, substituted cycloalkyl, substituted $C_6$–$C_{12}$aryl, aryloxy, hydroxy, alkoxy, cycloalkyl, amino, nitro, cyano, halogen and protected —OH; and pharmaceutically acceptable salts, hydrates, solvates and esters thereof.

The most preferred among the presently invented Formula I compounds are those in which R and $R^{20}$ are hydrogen; X and Y are independently selected from sulfur, oxygen, an amino group which may be substituted by $C_1$–$C_{10}$alkyl, benzyl or phenyl; $R^1$ and $R^2$ are each independently selected from $C_{1-6}$alkoxy, $C_{1-6}$alkyl and phenyl; and $R^3$ and $R^4$ are each independently phenyl or phenyl optionally substituted with from one to three substituents selected from the group consisting of: carboxylic acid, sulfonic acid, alkyl, substituted alkyl, hydroxy, alkoxy and halogen; and pharmaceutically acceptable salts, hydrates, solvates and esters thereof.

Preferred among the presently invented compounds are

4-{3-methyl-4-[1-(3,4-dimethylphenyl)-3-methyl-5-oxo-2-pyrazolin-4-ylazo]-5-oxo-2-pyrazolin-1-yl}benzoic acid;

4-{3-methyl-4-[3-methyl-5-oxo-1-(3-trifluoromethylphenyl)-2-pyrazolin-4-ylazo]-5-oxo-2-pyrazolin-1-yl}benzoic acid;

4-{3-methyl-4-[1-(4-iodophenyl)3-methyl-5-oxo-2-pyrazolin-4-ylazo]-5-oxo-2-1-yl}benzoic acid;

4-{3-methyl-[1-(3,4-dichlorophenyl)-3-methyl-5-oxo-1)-2-pyrazolin-4-ylazo]-5-oxo-2-pyrazolin-1-yl}benzoic acid;

4-{3-methyl-4-[3-methyl-5-oxo-1-(quinolin-2-yl)-2-pyrazolin-4-ylazo]-5-oxo-2-pyrazolin-1-yl}benzoic acid;

4-{3-methyl-4-[1-(4-tert-butylphenyl)3-methyl-5-oxo-2-pyrazolin-4-ylazo]-2-pyrazolin-1-yl}benzoic acid;

3-{3-methyl-4-[1-(3,4-dimethylphenyl)-3-methyl-5-oxo-2-pyrazolin-4-ylazo]-5-oxo-2-pyrazolin-1-yl}benzoic acid;

3-{3-methyl-4-[3-methyl-5-oxo-1-(3-trifluoromethylphenyl)-2-pyrazolin-4-ylazo]-5-oxo-2-pyrazolin-1-yl}benzoic acid;

3-{3-methyl-4-[1-(4-iodophenyl)3-methyl-5-oxo-2-pyrazolin-4-ylazo]-5-oxo-2-pyrazolin-1-yl}benzoic acid;

3-{3-methyl-4-[1-(3,4-dichlorophenyl)-3-methyl-5-oxo-1)-2-pyrazolin-4-ylazo]-pyrazolin-1-yl}benzoic acid;

3-{3-methyl-4-[3-methyl-5-oxo-1-(quinolin-2-yl)-2-pyrazolin-4-ylazo]-5-oxo-2-pyrazolin-1-yl}benzoic acid;

3-{3-methyl-4-[1-(4-tert-butylphenyl)3-methyl-5-oxo-2-pyrazolin-4-ylazo]-5-oxo-2-pyrazolin-1-yl}benzoic acid;

2-{3-methyl-4-[1-(3,4-dimethylphenyl)-3-methyl-5-oxo-2-pyrazolin-4-ylazo]-5-oxo-2-pyrazolin-1-yl}acetic acid;

2-{3-methyl-4-[3-methyl-5-oxo-1-(3-trifluoromethylphenyl)-2-pyrazolin-4-ylazo]-5-oxo-2-pyrazolin-1-yl}acetic acid;

2-{3-methyl-4-[1-(3,4-dichlorophenyl)-3-methyl-5-oxo-1)-2-pyrazolin-4-ylazo]-5-oxo-2-pyrazolin-1-yl}acetic acid; and 2-{3-methyl-4-[1-(4-tert-butylphenyl)3-methyl-5-oxo-2-pyrazolin-4-ylazo]-5-oxo-2-pyrazolin-1-yl}acetic acid.

Compounds of Formula (I) are included in the pharmaceutical compositions of the invention and used in the methods of the invention.

By the term "protected hydroxy" or "protected —OH" as used herein, is meant the alcoholic or carboxylic —OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "$C_6$–$C_{12}$aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: —$CO_2R^{25}$, aryl, —$C(O)NHS(O)_2R^{25}$, —$NHS(O)_2R^{25}$, hydroxyalkyl, alkoxy, —$C(O)NR^{21}R^{22}$, acyloxy, alkyl, amino, N-acylamino, hydroxy, —$(CH_2)_gC(O)OR^{26}$, —$S(O)_nR^{26}$, nitro, tetrazole, cyano, oxo, halogen, trifluoromethyl and protected —OH, where g is 0–6, $R^{26}$ is hydrogen or alkyl, $R^{25}$ is selected form hydrogen, $C_1$–$C_4$alkyl, aryl and trifluoromethyl, and $R^{21}$ and $R^{22}$ are independently selected form hydrogen, $C_1$–$C_4$alkyl, aryl and trifluoromethyl, and n is 0–2.

By the term "alkoxy" as used herein is meant —Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$–$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^{13}$, —$S(O)_nR^{14}$, nitro, cyano, halogen and protected —OH, where g is 0–6, $R^{13}$ is hydrogen or alkyl, n is 0–2 and $R^{14}$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —$CH_3$, —$CH_2$—$CH_3$, —$CH_2$—$CH_2$—$CH_3$, —CH($CH_3$)$_2$, —C($CH_3$)$_3$, —($CH_2$)$_3$—$CH_3$, —$CH_2$—CH($CH_3$)$_2$, —CH($CH_3$)—$CH_2$—$CH_3$, —CH═$CH_2$, and —C≡C—$CH_3$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The novel compounds of Formula I are prepared as shown in Scheme I below, or by analogous methods, wherein X, Y, R, $R^1$, $R^2$, $R^3$, $R^4$ and $R^{20}$ are as defined in Formula I and provided that the "R", X, and Y substituents do not include any such substituents that render inoperative the Scheme I process. All of the starting materials are commercially available or are readily made from commercially available starting materials by those of skill in the art.

Scheme I

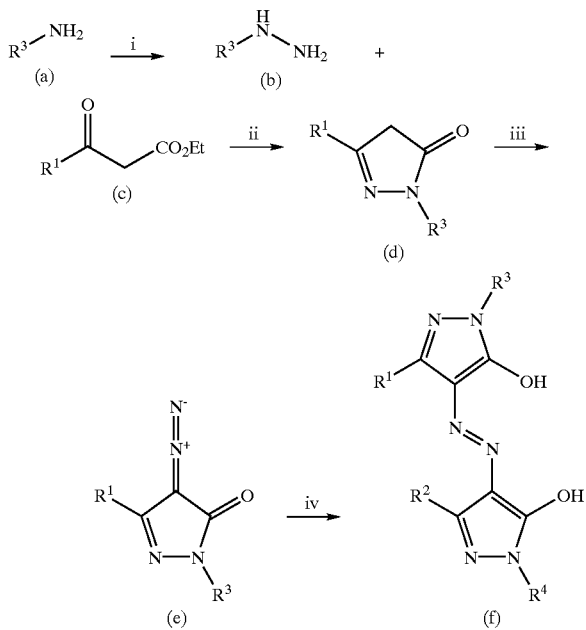

i) $NaNO_2$, HCl, water then $SnCl_2$, water; ii) AcOH, heat, iii) 4-$CH_3$—($C_6H_4$)—$SO_2N_3$, $Et_3N$, MeOH; iv) pyrazole, $Et_3N$, EtOH Scheme I outlines the formation of compounds of formula (I) where R is H and X is O. Compounds of formula (1) where R is not H and X is not O can be made by analogous methods well known to those of skill in the art. An amine such as 4-aminobenzoic acid or 3,4-dimethylaniline, compound (a), is diazotized by the action of sodium nitrite and an appropriate acid such as hydrochloric acid, nitric acid or sulfuric acid in an appropriate aqueous solvent system such as water or ethanol-water mixtures then reduced in situ by tin chloride to afford hydrazine, compound (b). The hydrazine is then condensed with a beta-keto ester such as ethyl acetoacetate, compound (c), in an appropriate solvent such as acetic acid or ethanol at an appropriate temperature typically 0–1000 to give the corresponding pyrazole, compound (d). The pyrazole (d) is then treated with a sulfonyl azide such as p-toluenesulfonyl azide in the presence of a base typically triethylamine or pyridine in a suitable solvent such as ethanol, methanol or tetrahydrofuran to afford diazopyrazole (e). Compound (f) is then formed by the reaction of diazo compound (e) in a coupling reaction with an appropriate pyrazole (d) in the presence of a base, preferably triethylamine or sodium hydrogen carbonate, or an acid, preferably hydrochloric acid in an appropriate solvent such as ethanol.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

Luciferase Assay

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells.

Some of the most preferred compounds of this invention were also active in an in vitro proliferation assay using the murine 32D-mpl cell line (Bartley, T. D. et al., Cell, 1994, 77, 1117–1124). 32D-mpl cells express Tpo-R and their survival is dependent on the presence of TPO. Likewise, some of the most preferred compounds of this invention were also positive in stimulating the maturation of megakaryocytes from human bone marrow cells. In this assay, purified human CD34[+] progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696–1699).

The pharmaceutically active compounds within the scope of this invention are useful as TPO mimetics in mammals, including humans, in need thereof.

Some of the preferred compounds within the scope of the invention showed activation from about 4% to 100% control at a concentration of 0.03–30 uM in the luciferase assay. The preferred compounds of the invention also promoted the proliferation of 32D-mpl cells at a concentration of 0.03 to 30 uM. The preferred compounds of the invention also showed activity in the CD41 megakaryocytic assay at a concentration of 0.03 to 30 uM.

The present invention therefor provides a method of treating thrombocytopenia and other conditions with depressed platelet production, which comprises administering a compound of Formula (I), as described above, or a pharmaceutically acceptable salts, hydrates, solvates and esters thereof, in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (1) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formula I may also exist in tautomeric forms, wherein the double bond that is drawn between the two nitrogen atoms exists between the lower nitrogen atom and the lower pyrazole ring or the double bond can exist between the upper nitrogen atom and the upper pyrazole ring or double bonds can exist both between the lower nitrogen atom and the lower pyrazole ring and the upper nitrogen atom and the upper pyrazole ring. Tautomeric forms of the compounds of Formula I are exemplified by the following Formulae II, III and IV:

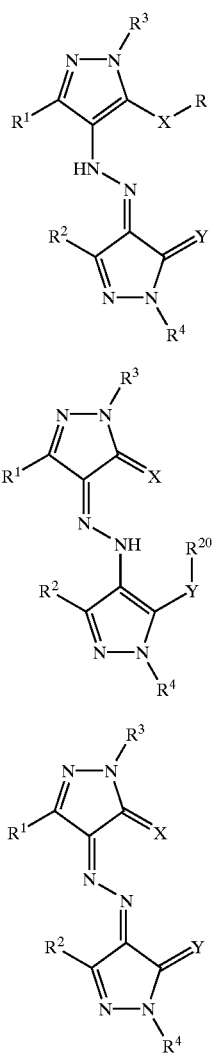

(II)

(III)

(IV)

where the 'R' groups are as defined above. All such compounds are included in the scope of the invention and inherently included in the definition of the compounds of Formula I.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

EXAMPLE 1

Preparation of 4-[1-(3,4-Dimethylphenyl)-3-methyl-4-(3-methyl-5-oxo-2-pyrazolin-4-ylazo)-5-oxo-2-pyrazolin-1-yl]benzoic Acid a) 1-(3,4-Dimethylphenyl)-3-methyl-3-pyrazolin-5-one A solution of 3,4-dimethylphenylhydrazine (7.3 g; 0.053 mol.) and ethyl acetoacetate (6.9 g; 0.053 mol.) in glacial acetic acid (50.0 mL) was stirred and heated at 100° for 24h. The solvent was evaporated and the product purified by chromatography (silica gel, 50% ethyl acetate/hexanes) to afford the title compound (16.8 g; 64%). MS(ES) m/z 203 [M+H].

b) 4-(4-Diazo-3-methyl-5-oxo-2-pyrazolin-1-yl)benzoic Acid

A solution of 4-(3-methyl-5-oxo-2-pyrazolin-1-yl) benzoic acid (5.0 g, 0.023 mol) and p-toluenesulfonylazide (5.03 g, 0.026 mol) in methanol (30.0 mL) was treated with triethylamine (5.2 g; 0.051 mol.) and the reaction was stirred at room temperature for 5 hours.

The reaction was concentrated and treated with 1M aqu. hydrochloric acid (100 mL) and ethyl acetate (100 mL). The resulting precipitate was collected and dried to afford the title compound (3.4 g, 61%) as a yellow powder. MS(ES) m/z 245 [M+H]$^+$.

c) 4-[1-(3,4-Dimethylphenyl)-3-methyl-4-(3-methyl-5-oxo-2-pyrazolin-4-ylazo)-5-oxo-2-pyrazolin-1-yl]benzoic Acid A solution of the compound from Example 1a) (0.0366 g; 0.15 mmol.) and the compound from Example 1b) (0.0303 g; 0.15 mmol.) in ethanol (2.5 mL) was treated with triethylamine (0.10 mL) and stirred at room temperature overnight.

The mixture was evaporated and treated with 1M aqu. hydrochloric acid (10 mL) and a solid collected. Purification by chromatography [ODS, step gradient, 1–90% acetonitrile:water (0.1% TFA)] afforded the title compound as an orange powder (57.5 mg; 86%). MS(ES) m/z 447 [M+H]$^+$.

EXAMPLE 2

Preparation of 4-{3-Methyl-4-[3-methyl-5-oxo-1-(3-trifluoromethylphenyl)-2-pyrazolin-4-ylazo]-5-oxo-2-pyrazolin-1-yl}benzoic Acid a) 3-Methyl-1-(3-trifluoromethylphenyl)-3-pyrazolin-5-one Following the procedure of Example 1a), except substituting 3-trifluoromethylphenylhydrazine for 3,4-dimethylphenylhydrazine, the title compound was prepared (0.78 g; 76%). MS(ES) m/z 243 [M+H].

b) 4-{3-Methyl-4-[3-methyl-5-oxo-1-(3-trifluoromethylphenyl)-2-pyrazolin-4-ylazo]-5-2-pyrazolin-1-yl}benzoic Acid Following the procedure of Example 1c) except substituting the compound from Example 2a) for 1-(3,4-dimethylphenyl)-3-methyl-3-pyrazolin-5-one, the title compound was prepared as an orange powder (10.0 mg; 14%). MS(ES) m/z 487 [M+H]$^+$.

EXAMPLE 3

Preparation of 4-{3-Methyl-4-[1-(4-iodophenyl)3-methyl-5-oxo-2-pyrazolin-4-ylazo]-5-oxo-2-pyrazolin-1-yl}benzoic Acid a) 1-(4-Iodophenyl)-3-methyl-3-pyrazolin-5-one Following the procedure of Example 1a), except substituting 4-iodophenylhydrazine for 3,4-dimethylphenylhydrazine, the title compound was prepared (0.60 g; 17%). MS(ES) m/z 301 [M+H].

b) 4-{3-Methyl-4-[1-(4-iodophenyl)3-methyl-5-oxo-2-pyrazolin-4-ylazo]-5-oxo-2-pyrazolin-1-yl}benzoic Acid Following the procedure of Example 1c) except substituting the compound from Example 3a) for 1-(3,4-dimethylphenyl)-3-methyl-3-pyrazolin-5-one, the title compound was prepared as an orange powder (10.0 mg; 12%). MS(ES) m/z 545 [M+H]$^+$.

EXAMPLE 4

Preparation of 4-{3-Methyl-4-[1-(3,4-dichlorophenyl)-3-methyl-5-oxo-2-pyrazolin-4-ylazo]-5-oxo-2-pyrazolin-1-yl}benzoic Acid a) 1-(3,4-Dichlorophenyl)-3-methyl-3-pyrazolin-5-one Following the procedure of Example 1a), except substituting 3,4-dichlorophenylhydrazine for 3,4- dimethylphenylhydrazine, the title compound was prepared (5.0 g; 77%). MS(ES) m/z 244 [M+H].

b) 4-{3-Methyl-4-[1-(3,4-dichlorophenyl)-3-methyl-5-oxo-1)-2-pyrazolin-4-ylazo]-5-oxo-2-pyrazolin-1-yl}benzoic Acid Following the procedure of Example 1c) except substituting the compound from Example 4a) for 1-(3,4-dimethylphenyl)-3-methyl-3-pyrazolin-5-one, the title compound was prepared as an orange powder (5.0 mg; 7%). MS(ES) m/z 488 [M+H]$^+$.

EXAMPLE 5

Preparation of 4-{3-Methyl-4-[3-methyl-5-oxo-1-(quinolin-2-yl)-2-pyrazolin-4-ylazo]-5-oxo-2-pyrazolin-1-yl}benzoic Acid a) 3-Methyl-1-(quinolin-2-yl)-3-pyrazolin-5-one Following the procedure of Example 1a), except substituting 2-hydrazinoquinoline for 3,4-dimethylphenylhydrazine, the title compound was prepared (0.84 g; 56%). MS(ES) m/z 226 [M+H].

b) 4-{3-Methyl-4-[3-methyl-5-oxo-1-(quinolin-2-yl)-2-pyrazolin-4-ylazo]-5-oxo-2-pyrazolin-1-yl}benzoic Acid Following the procedure of Example 1c) except substituting the compound from Example 5a) for 1-(3,4-dimethylphenyl)-3-methyl-3-pyrazolin-5-one, the title compound was prepared as an orange powder (5.0 mg; 7%). MS(ES) m/z 470 [M+H]$^+$.

EXAMPLE 6

Preparation of 4-{3-Methyl-4-[1-(4-tert-butylphenyl)3-methyl-5-oxo-2-pyrazolin-4-ylazo]-5-oxo-2-pyrazolin-1-yl}benzoic Acid a) 1-(4-tert-Butylphenyl)-3-methyl-3-pyrazolin-5-one Following the procedure of Example 1a), except substituting 4-tert-butlyphenylhydrazine for 3,4-dimethylphenylhydrazine, the title compound was prepared (4.6 g; 73%). MS(ES) m/z 231 [M+H].

b) 4-{3-Methyl-4-[1-(4-tert-butylphenyl)3-methyl-5-oxo-2-pyrazolin-4-ylazo]-5-oxo-2-pyrazolin-1-yl}benzoic Acid Following the procedure of Example 1c) except substituting the compound from Example 6a) for 1-(3,4-dimethylphenyl)-3-methyl-3-pyrazolin-5-one, the title compound was prepared as an orange powder (12.0 mg: 17%). MS(ES) m/z 474 [M+H]$^+$.

EXAMPLE 7

Preparation of 3-{3-Methyl-4-[1-(3,4-dimethylphenyl)-3-methyl-5-oxo-2-pyrazolin-4-ylazo]-5-oxo-2-pyrazolin-1-yl}benzoic Acid a) 3-(3-Methyl-5-oxo-2-pyrazolin-1-yl)benzoic Acid Following the procedure of Example 1a), except substituting 3-hydrazinobenzoic acid for 3,4-dimethylphenylhydrazine, the title compound was prepared (13.7 g; 96%). MS(ES) m/z 219 [M+H].

b) 3-(4-Diazo-3-methyl-5-oxo-2-pyrazolin-1-yl)benzoic Acid

Following the procedure of Example 1b), except substituting the compound from Example 7a) for 4-(3-methyl-5-oxo-2-pyrazolin-1-yl)benzoic acid, the title compound was prepared as a yellow powder (4.5 g; 81%). MS(ES) m/z 245 [M+H].

c) 3-[1-(3,4-Dimethylphenyl)-3-methyl-4-(3-methyl-5-oxo-2-pyrazolin-4-ylazo)-5-oxo-2-pyrazolin-1-yl]benzoic Acid Following the procedure of Example 1c), except substituting the compound from Example 7b) for 4-(4-diazo-3-methyl-5-oxo-2-pyrazolin-1-yl)benzoic acid, the title compound was prepared as an orange powder (11.0 mg; 16%). MS(ES) m/z 447 [M+H]$^+$.

EXAMPLE 8

Preparation of 3-{3-Methyl-4-[3-methyl-5-oxo-1-(3-trifluoromethylphenyl)-2-pyrazolin-4-ylazo]-5-oxo-2-pyrazolin-1-yl}benzoic Acid Following the procedure of Example 1c), except substituting the compound from Example 7b) for 4-(4-diazo-3-methyl-5-oxo-2-pyrazolin-1-yl)benzoic acid and the compound from Example 2a),for 3,4-dimethylphenylhydrazine, the title compound was prepared as an orange powder (10.0 mg; 14%). MS(ES) m/z 487 [M+H]$^+$.

EXAMPLE 9

Preparation of 3-{3-Methyl-4-[1-(4-iodophenyl)3-methyl-5-oxo-2-pyrazolin-4-ylazo]-5-oxo-2-pyrazolin-1-yl}benzoic Acid Following the procedure of Example 1c), except substituting the compound from Example 7b) for 4-(4-diazo-3-methyl-5-oxo-2-pyrazolin-1-yl)benzoic acid and the compound from Example 3a) for 3,4-dimethylphenylhydrazine, the title compound was prepared as an orange powder (8.0 mg; 10%). MS(ES) m/z 545 [M+H]$^+$.

EXAMPLE 10

Preparation of 3-{3-Methyl-4-[1-(3,4-dichlorophenyl)-3-methyl-5-oxo-1)-2-pyrazolin-4-ylazo]-5-oxo-2-pyrazolin-1-yl}benzoic Acid Following the procedure of Example 1c), except substituting the compound from Example 7b) for 4-(4-diazo-3-methyl-5-oxo-2-pyrazolin-1-yl)benzoic acid and the compound from Example 4a) for 3,4-dimethylphenylhydrazine, the title compound was prepared as an orange powder (8.0 mg; 11%). MS(ES) m/z 488 [M+H]$^+$.

EXAMPLE 11

Preparation of 3-{3-Methyl-4-[3-methyl-5-oxo-1-(quinolin-2-yl)-2-pyrazolin-4-ylazo]-5-oxo-2-pyrazolin-1-yl}benzoic Acid Following the procedure of Example 1c), except substituting the compound from Example 7b) for 4-(4-diazo-3-methyl-5-oxo-2-pyrazolin-1-yl)benzoic acid and the compound from Example 5a) for 3,4-dimethylphenylhydrazine, the title compound was prepared as an orange powder (4.0 mg; 6%). MS(ES) m/z 470 [M+H]$^+$.

EXAMPLE 12

Preparation of 3-{3-Methyl-4-[1-(4-tert-butylphenyl)3-methyl-5-oxo-2-pyrazolin-4-ylazo]-5-oxo-2-pyrazolin-1-yl}benzoic Acid Following the procedure of Example 1c), except substituting the compound from Example 7b) for 4-(4-diazo-3-methyl-5-oxo-2-pyrazolin-1-yl)benzoic acid and the compound from Example 6a) for 3,4-dimethylphenylhydrazine, the title compound was prepared as an orange powder (15.0 mg; 21%). MS(ES) m/z 475 [M+H]$^+$.

EXAMPLE 13

Preparation of 2-{3-Methyl-4-[1-(3,4-dimethylphenyl)-3-methyl-5-oxo-2-pyrazolin-4-ylazo]-5-oxo-2-pyrazolin-1-yl}acetic Acid a) 2-(3-Methyl-5-oxo-2-pyrazolin-1-yl)acetic Acid Following the procedure of Example 1a), except substituting ethyl 2-hydrazinoacetate hydrochloride for 3,4-dimethylphenylhydrazine, the title compound was prepared (2.24 g; 63%). MS(ES) m/z 157 [M+H].

b) 2-(4-Diazo-3-methyl-5-oxo-2-pyrazolin-1-yl)acetic Acid

Following the procedure of Example 1b), except substituting the compound from Example 13a) for 4-(3-methyl-5-oxo-2-pyrazolin-1-yl)benzoic acid, the title compound was prepared as a yellow powder. MS(ES) m/z 183 [M+H].

c) 3-[1-(3,4-Dimethylphenyl)-3-methyl-4-(3-methyl-5-oxo-2-pyrazolin-4-ylazo)5-oxo-2-pyrazolin-1-yl]benzoic Acid Following the procedure of Example 1c), except substituting the compound from Example 13b) for 4-(4-diazo-3-methyl-5-oxo-2-pyrazolin-1-yl)benzoic acid, the title compound was prepared as an orange powder (22.5 mg; 39%). MS(ES) m/z 385 [M+H]$^+$.

EXAMPLE 14

Preparation of 2-{3-Methyl-4-[3-methyl-5-oxo-1-(3-trifluoromethylphenyl)-2-pyrazolin-4-ylazo]-5-oxo-2-pyrazolin-1-yl}acetic Acid Following the procedure of Example 1c), except substituting the compound from Example 13b) for 4-(4-diazo-3-methyl-5-oxo-2-pyrazolin-1-yl)benzoic acid and the compound from Example 2a) for 3,4-dimethylphenylhydrazine, the title compound was prepared as an orange powder (2.0 mg; 3%). MS(ES) m/z 425 [M+H]$^+$.

EXAMPLE 15

Preparation of 2-{3-Methyl-4-[1-(3,4-dichlorophenyl)-3-methyl-5-oxo-1)2-pyrazolin-4-ylazo]-5-oxo-2-pyrazolin-1-yl}acetic Acid Following the procedure of Example 1c), except substituting the compound from Example 13b) for 4-(4-diazo-3-methyl-5-oxo-2-pyrazolin-1-yl)benzoic acid and the compound from Example 4a) for 3,4-dimethylphenylhydrazine, the title compound was prepared as an orange powder (2.0 mg; 3%). MS(ES) m/z 426 [M+H]$^+$.

EXAMPLE 16

Preparation of 2-{3-Methyl-4-[1-(4-tert-butylphenyl)3-methyl-5-oxo-2-pyrazolin-4-ylazo]-5-oxo-2-pyrazolin-1-yl}acetic Acid Following the procedure of Example 1c), except substituting the compound from Example 13b) for 4-(4-diazo-3-methyl-5-oxo-2-pyrazolin-1-yl)benzoic acid and the compound from Example 6a) for 3,4-dimethylphenylhydrazine, the title compound was prepared as an orange powder (2.0 mg; 3%). MS(ES) m/z 413 [M+H]$^+$.

EXAMPLE 17

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 4-[1-(3,4-dimethylphenyl)-3-methyl-4-(3-methyl-5-oxo)-2-pyrazolin-4-ylazo)-5-oxo-2-pyrazolin-1-yl]benzoic acid (Compound 1) | 25 mg |
| Lactose | 55 mg |
| Talc | 16 mg |
| Magnesium Stearate | 4 mg |

EXAMPLE 18

Injectable Parenteral Composition

An injectable form for administering a presently invented agonist of the TPO receptor is produced by stirring 1.5% by weight of 4-{3-methyl-4-[3-methyl-5-oxo-1-(3-trifluoromethylphenyl)-2-pyrazolin-4-ylazo]-5-oxo-2-pyrazolin-1-yl}benzoic acid (Compound 2) in 10% by volume propylene glycol in water.

EXAMPLE 19

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 4-{3-methyl-4-[1-(4-iodophenyl)3-methyl-5-oxo--2-pyrazolin-y-ylazo]-5-oxo-2-pyrazolin-1-yl}benzoic acid (Compound 3) | 20 mg |
| calcium sulfate dihydrate | 30 mg |
| sucrose | 4 mg |
| starch | 2 mg |
| talc | 1 mg |
| stearic acid | 0.50 mg |

Preferred among the compounds of the present invention are the compounds of Examples 1 and 10.

The compound of Example 1 demonstrated an activity of, EC50=0.72 uM, 56% TPO in the above luciferase assay.

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating of thrombocytopenia in a mammal in need thereof which comprises administering to such mammal a therapeutically effective amount of a compound of Formula (I),

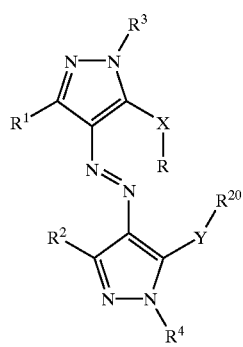

(I)

wherein:
X and Y are independently selected from sulfur, oxygen, an amino group which is optionally substituted by $C_1$–$C_{10}$alkyl, benzyl or phenyl;

R and $R^{20}$ is selected from hydrogen, alkyl, cycloalkyl, $C_1$–$C_{12}$aryl, substituted alkyl, substituted cycloalkyl and substituted $C_1$–$C_{12}$aryl;

$R^1$ and $R^2$ are each independently selected from hydrogen, alkyl, cycloalkyl, aryl, substituted alkyl, substituted cycloalkyl, substituted aryl, alkoxy, substituted alkoxy, —$(CH_2)_m OR^5$, sulfonic acid, —$COOR^5$, nitro, amino, —$NR^6R^7$, —N-acylamino, —$N(R^{10})C(O)R^{11}$, —$N(R^{10})C(O)NR^6R^7$, —$N(R^{10})SO_2R^{11}$, cyano, halogen, —$S(O)_n R^5$, protected —OH, —$CONR^6R^7$, phosphonic acid, phosphinic acid and —$SO_2NR^6R^7$, where
m is 0–6;

$R^5$ is selected from hydrogen, alkyl, cycloalkyl, $C_1$–$C_{12}$aryl, substituted alkyl, substituted cycloalkyl and substituted $C_1$–$C_{12}$aryl, $R^6$ and $R^7$ are each independently selected from hydrogen, alkyl, $C_3$–$C_6$cycloalkyl, phenyl, $C_1$–$C_{12}$aryl or $R^6$ and $R^7$ taken together with the nitrogen to which they are attached represent a 5 to 6 member saturated ring containing up to one other heteroatom selected from oxygen and nitrogen, $R^{10}$ and $R^{11}$ are each independently selected from hydrogen, alkyl, $C_3$–$C_6$cycloalkyl, phenyl, $C_1$–$C_{12}$aryl and
n is 0–2;

$R^3$ and $R^4$ are independently selected from alkyl, cycloalkyl, substituted alkyl, substituted cycloalkyl, —$(CH_2)_m COOR^5$ and a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, $C_1$–$C_{12}$aryl, substituted cycloalkyl, substituted $C_1$–$C_{12}$aryl, aryloxy, hydroxy, alkoxy, cycloalkyl, acyloxy, amino, N-acylamino, nitro, cyano, halogen, —$C(O)OR^{12}$, —$C(O)NR^8R^9$, —$S(O)_2NR^8R^9$, —$S(O)_n R^5$, protected —OH and alkyl substituted with one or more substituents selected from the group consisting of: alkoxy, acyloxy, $C_1$–$C_{12}$aryl, substituted $C_1$–$C_{12}$aryl, amino, N-acylamino, oxo, hydroxy, cycloalkyl, substituted cycloalkyl, —$C(O)OR^{12}$, —$S(O)_2NR^8R^9$, —$S(O)_n R^5$, aryloxy, nitro, cyano, halogen, and protected —OH, where m is 0–6,
$R^5$ is as described above,
$R^8$ and $R^9$ are independently selected form hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —$C(O)OR^5$, —$S(O)_n R^5$, $C(O)NR^5R^5$, $S(O)_2NR^5R^5$, nitro, cyano, cycloalkyl, substituted cycloalkyl, halogen, $C_1$–$C_{12}$aryl, substituted $C_1$–$C_{12}$aryl and protected —OH where $R^5$ and n are as described above, or $R^8$ and $R^9$ taken together with the nitrogen to which they are attached represent a 5 to 6 member saturated ring containing up to one other heteroatom selected from oxygen and nitrogen, $R^{12}$ is selected form hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —$C(O)OR^5$, —$S(O)_n R^5$, $C(O)NR^5R^5$, $S(O)_2NR^5R^5$, nitro, cyano, cycloalkyl, substituted cycloalkyl, halogen, $C_1$–$C_{12}$aryl, substituted $C_1$–$C_{12}$aryl and protected —OH where $R^5$ and n are as described above, and
n is 0–2; and pharmaceutically acceptable salts, hydrates, solvates and esters thereof.

2. The method of claim 1 in which the mammal is a human.

3. The method of claim 2 in which the compound of Formula (I) is selected from:

4-{3-methyl-4-[1-(3,4-dimethyl phenyl)-3-methyl-5-oxo-2-pyrazolin-4-ylazo]-5-oxo-2-pyrazolin-1-yl}benzoic acid;

4-{3-methyl-4-[3-methyl-5-oxo-1-(3-trifluoromethylphenyl)-2-pyrazolin-4-ylazo]-5-oxo-2-pyrazolin-1-yl}benzoic acid;

4-{3-methyl-4-[1-(4-iodophenyl)3-methyl-5-oxo-2-pyrazolin-4-ylazo]-5-oxo-2-pyrazolin-1-yl}benzoic acid;

4-{3-methyl-4-[1-(3,4-dichlorophenyl)-3-methyl-5-oxo-1)-2-pyrazolin-4-ylazo]-5-oxo-2-pyrazolin-1-yl}benzoic acid;

4-{3-methyl-4-[3-methyl-5-oxo-1-(quinolin-2-yl)-2-pyrazolin-4-ylazo]-5-oxo-2-pyrazolin-1-yl}benzoic acid;

4-{3-methyl-4-[1-(4-tert-butylphenyl)3-methyl-5-oxo-2-pyrazolin-4-ylazo]-5-oxo-2-pyrazolin-1-yl}benzoic acid;

3-{3-methyl-4-[1-(3,4-dimethylphenyl)-3-methyl-5-oxo-2-pyrazolin-4-ylazo]-5-oxo-2-pyrazolin-1-yl}benzoic acid;

3-{3-methyl-4-[3-methyl-5-oxo-1-(3-trifluoromethylphenyl)-2-pyrazolin-4-ylazo]-5-oxo-2-pyrazolin-1-yl}benzoic acid;

3-{methyl-4-[1-(iodophenyl)3-methyl-5-oxo-2-pyrazol-4-ylazo]-oxo-2-pyrazolin-1-yl}benzoic acid;

3-{3-methyl-4-[1-(3,4-dichlorophenyl)-3-methyl-5-oxo-1)-2-pyrazolin-4-ylazo]-5-oxo-2-pyrazolin-1-yl}benzoic acid;

3-{3-methyl-4-[3-methyl-5-oxo-1-(quinolin-2-yl)-2-pyrazolin-4-ylazo]-5-oxo-2-pyrazolin-1-yl}benzoic acid;

3-{3-methyl-4-[1-(4-tert-butylphenyl)3-methyl-5-oxo-2-pyrazolin-4-ylazo]-5-oxo-2-pyrazolin-1-yl}benzoic acid;

2-{3-methyl-4-[1-(3,4-dimethylphenyl)-3-methyl-5-oxo-2-pyrazolin-4-ylazo]-5-oxo-2-pyrazolin-1-yl}acetic acid;

2-{3-methyl-4-[3-methyl-5-oxo-1-(3-trifluoromethylphenyl)-2-pyrazolin-4-ylazo]-5-oxo-2-pyrazolin-1-yl}acetic acid;

2-{3-methyl-4-[1-(3,4-dichlorophenyl)-3-methyl-5-oxo-1)-2-pyrazolin-4-ylazo]-5-oxo-2-pyrazolin-1-yl}acetic acid; and 2-{3-methyl-4-[1-(4-tert-butylphenyl)3-methyl-5-oxo-2-pyrazolin-4-ylazo]-5-oxo-2-pyrazolin-1-yl}acetic acid;

or a pharmaceutical acceptable salt, hydrate, solvate or ester thereof.

4. A method of enhancing platelet production in a mammal in need thereof which comprises administering to such mammal a therapeutically effective amount of a compound of Formula (I),

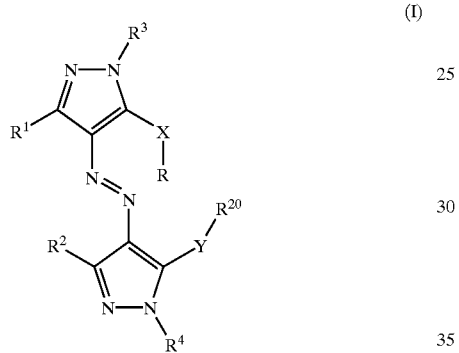

wherein:

X and Y are independently selected from sulfur, oxygen, an amino group which is optionally substituted by $C_1$–$C_{10}$alkyl, benzyl or phenyl;

R and $R^{20}$ is selected from hydrogen, alkyl cycloalkyl, $C_1$–$C_{12}$aryl, substituted alkyl substituted cycloalkyl and substituted $C_1$–$C_{12}$aryl;

$R^1$ and $R^2$ are each independently selected from hydrogen, alkyl, cycloalkyl, aryl, substituted alkyl, substituted cycloalkyl, substituted aryl, alkoxy, substituted alkoxy, $(CH_2)_mOR^5$, sulfonic acid, —$COOR^5$, nitro, amino, —$NR^6R^7$, N-acylamino, —$N(R^{10})C(O)R^{11}$, —$N(R^{10})C(O)NR^6R^7$, —$N(R^{10})SO_2R^{11}$, cyano, halogen, $S(O)_nR^5$, protected —OH, —$CONR^6R^7$, phosphonic acid, phosphinic acid and —$SO_2NR^6R^7$, where
m is 0–6;

$R^5$ is selected from hydrogen, alkyl, cycloalkyl, $C_1$–$C_{12}$aryl, substituted alkyl substituted cycloalkyl and substituted $C_1$–$C_{12}$aryl, $R^6$ and $R^7$ are each independently selected from hydrogen, alkyl, $C_3$–$C_6$cycloalkyl, phenyl, $C_1$–$C_{12}$aryl or $R^6$ and $R^7$ taken together with the nitrogen to which they are attached represent a 5 to 6 member saturated ring containing up to one other heteroatom selected from oxygen and nitrogen, $R^{10}$ and $R^{11}$ are each independently selected from hydrogen, alkyl, $C_3$–$C_6$cycloalkyl, phenyl, $C_1$–$C_{12}$aryl and
n is 0–2;

$R^3$ and $R^4$ are independently selected from alkyl, cycloalkyl, substituted alkyl, substituted cycloalkyl, —$(CH_2)_mCOOR^5$ and a cyclic or polycyclic aromatic ring containing from 3 to 16 carbon atoms and optionally containing one or more heteroatoms, provided that when the number of carbon atoms is 3 the aromatic ring contains at least two heteroatoms and when the number of carbon atoms is 4 the aromatic ring contains at least one heteroatom, and optionally substituted with one or more substituents selected from the group consisting of: alkyl, $C_1$–$C_{12}$aryl, substituted cycloalkyl, substituted $C_1$–$C_{12}$aryl, aryloxy, hydroxy, alkoxy, cycloalkyl, acyloxy, amino, N-acylamino, nitro, cyano, halogen, —$C(O)OR^{12}$, —$C(O)NR^8R^9$, —$S(O)_2NR^8R^9$, —$S(O)_nR^5$, protected —OH and alkyl substituted with one or more substituents selected from the group consisting of: alkoxy, acyloxy, $C_1$–$C_{12}$aryl, substituted $C_1$–$C_{12}$aryl, amino, N-acylamino, oxo, hydroxy, cycloalkyl, substituted cycloalkyl, —$C(O)OR^{12}$, —$S(O)_2NR^8R^9$, —$S(O)_nR^5$, aryloxy, nitro, cyano, halogen, and protected —OH, where
m is 0–6, $R^5$ is as described above, $R^8$ and $R^9$ are independently selected form hydrogen, cycloalkyl, $C_1$–$C_{12}$aryl, substituted cycloalkyl, substituted $C_{1-12}$aryl, alkyl or alkyl substituted with one or more substituents selected from the group consisting of: alkoxy, acyloxy, aryloxy, amino, N-acylamino, oxo, hydroxy, —$C(O)OR^5$, —$S(O)_nR^5$, $C(O)NR^5R^5$, $S(O)_2NR^5R^5$, nitro, cyano, cycloalkyl, substituted cycloalkyl, halogen, $C_1$–$C_{12}$aryl, substituted $C_1$–$C_{12}$aryl and protected —OH where $R^5$ and n are as described above, or $R^8$ and $R^9$ taken together with the nitrogen to which they are attached represent a 5 to 6 member saturated ring containing up to one other heteroatom selected from oxygen and nitrogen, $R^{12}$ is selected form hydrogen, cycloalkyl, $C_1$–$C_{12}$aryl, substituted cycloalkyl, substituted $C_1$–$C_{12}$aryl, alkyl or alkyl substituted with one or more substituents selected from the group consisting of: alkoxy, acyloxy, aryloxy, amino, N-acylamino, oxo, hydroxy, —$C(O)OR^5$, —$S(O)_nR^5$, $C(O)NR^5R^5$, $S(O)_2NR^5R^5$, nitro, cyano, cycloalkyl, substituted cycloalkyl, halogen, $C_1$–$C_{12}$aryl, substituted $C_1$–$C_{12}$aryl and protected —OH where $R^5$ and n are as described above, and n is 0–2; and pharmaceutically acceptable salts, hydrates, solvates and esters thereof.

5. The method of claim 4 in which the mammal is a human.

6. The method of claim 5 in which the compound of Formula (I) is selected from:

4-{3-methyl-4-[1-(3,4-dimethylphenyl)-3-methyl-5-oxo-2-pyrazolin-4-ylazo]-5-oxo-2-pyrazolin-1-yl}benzoic acid;

4-{3-methyl-4-[3-methyl-5-oxo-1-(3-trifluoromethylphenyl)-2-pyrazolin-4-ylazo]-5-oxo-pyrazolin-1-yl}benzoic acid;

4-{3-methyl-4-[1-(4-iodophenyl)3-methyl-5-oxo-2-pyrazolin-4-ylazo]-5-oxo-pyrazolin-1-yl}benzoic acid;

4-{3-methyl-4-[1-(3,4-dichlorophenyl)-3-methyl-5-oxo-1)-2-pyrazolin-4-ylazo]-5-oxo-2-pyrazolin-1-yl}benzoic acid;

4-{3-methyl-4-[3-methyl-5-oxo-1-(quinolin-2-yl)-2-pyrazolin-4-ylazo]-5-oxo-2-pyrazolin-1 1-yl}benzoic acid;

4-{3-methyl-4-[1-(4-tert-butylphenyl)3-methyl-5-oxo-2-pyrazolin-4-ylazo]-5-oxo-pyrazolin-1-yl}benzoic acid;

3-{3-methyl-4-[1-(3,4-dimethylphenyl)-3-methyl-5-oxo-2-pyrazolin-4-ylazo]-5-oxo-2-pyrazolin-1-yl}benzoic acid;

3-{3-methyl-4-[3-methyl-5-oxo-1-(3-trifluoromethylphenyl)-2-pyrazolin-4-ylazo]-5-oxo-2-pyrazolin-1-yl}benzoic acid;

3-{3-methyl-4-[1-(4-iodophenyl)3-methyl-5-oxo-2-pyrazolin-4-ylazo]-5-oxo-2-pyrazolin-1-yl}benzoic acid;

3-{3-methyl-4-[1-(3,4-dichlorophenyl)-3-methyl-5-oxo-1)-2-pyrazolin-4-ylazo]-5-oxo-2-pyrazolin-1-yl}benzoic acid;

3-{3-methyl-4-[3-methyl-5-oxo-1-(quinolin-2-yl)-2-pyrazolin-4-ylazo]-5-oxo-2-pyrazolin-1-yl}benzoic acid;

3-{3-methyl-4-[1-(4-tert-butylphenyl)3-methyl-5-oxo-2-pyrazolin-4-ylazo]-5-oxo-2-pyrazolin-1-yl}benzoic acid;

2-{3-methyl-4-[1-(3,4-dimethylphenyl)-3-methyl-5-oxo-2-pyrazolin-4-ylazo]-5-oxo-pyrazolin-1-yl}acetic acid;

2-{3-methyl-4-[3-methyl-5-oxo-1-(3-trifluoromethylphenyl)-2-pyrazolin-4-ylazo]-5-oxo-2-pyrazolin-1-yl}acetic acid;

2-{3-methyl-4-[1-(3,4-dichlorophenyl)-3-methyl-5-oxo-1)-2-pyrazolin-4-ylazo]-5-oxo-2-pyrazolin-1-yl}acetic acid; and 2-{3-methyl-4-[1-(4-tert-butylphenyl)3-methyl-5-oxo-2-pyrazolin-4-ylazo]-5-oxo-2-pyrazolin-1-yl}acetic acid;

or a pharmaceutical acceptable salt, hydrate, solvate or ester thereof.

7. The method of claim 1 wherein the compound is administered orally.

8. The method of claim 3 wherein the compound is administered parenterally.

9. A method of agonizing the TPO receptor in a mammal which comprises administering an effective amount of a compound of the Formula (I) as described in claim 1.

10. The method of claim 9 in which the mammal is a human.

11. A pharmaceutical composition which comprises a compound of the Formula (I) as described in claim 1 and a pharmaceutically acceptable carrier.

12. A pharmaceutical composition which comprises a pharmaceutically acceptable carrier and a compound selected from:

4-{3-methyl-4-[1-(3,4-dimethylphenyl)-3-methyl-5-oxo-2-pyrazolin-4-ylazo]-5-oxo-2-pyrazolin-1-yl}benzoic acid;

4-{3-methyl-4-[3-methyl-5-oxo-1-(3-trifluoromethylphenyl)-2-pyrazolin-4-ylazo]-5-oxo-2-pyrazolin-1-yl}benzoic acid;

4-{3-methyl-4-[1-(4-iodophenyl)3-methyl-5-oxo-2-pyrazolin-4-ylazo]-5-oxo-2-pyrazolin-1-yl}benzoic acid;

4-{3-methyl-4-[1-(3,4-dichlorophenyl)-3-methyl-5-oxo-1)-2-pyrazolin-4-ylazo]-5-oxo-2-pyrazolin-1-yl}benzoic acid;

4-{3-methyl-4-[3-methyl-5-oxo-1-(quinolin-2-yl)-2-pyrazolin-4-ylazo]-5-oxo-2-pyrazolin-1-yl}benzoic acid;

4-{3-methyl-4-[1-(4-tert-butylphenyl)3-methyl-5-oxo-2-pyrazolin-4-ylazo]-5-oxo-2-pyrazolin-1-yl}benzoic acid;

3-{3-methyl-4-[1-(3,4-dimethylphenyl)-3-methyl-5-oxo-2-pyrazolin-4-ylazo]-5-oxo-2-pyrazolin-1-yl}benzoic acid;

3-{3-methyl-4-[3-methyl-5-oxo-1-(3-trifluoromethylphenyl)-2-pyrazolin-4-ylazo]-5-oxo-2-pyrazolin-1-yl}benzoic acid;

3-{3-Methyl-4-[1-(4-iodophenyl)3-methyl-5-oxo-2-pyrazolin-4-ylazo]-5-oxo-2-pyrazolin-1-yl}benzoic acid;

3-{3-methyl-4-[1-(3,4-dichlorophenyl)-3-methyl-5-oxo-1)-2-pyrazolin-4-ylazo]-5-oxo-2-pyrazolin-1-yl}benzoic acid;

3-{3-methyl-4-[3-methyl-5-oxo-1-(quinolin-2-yl)-2-pyrazolin-4-ylazo]-5-oxo-2-pyrazolin-1-yl}benzoic acid;

3-{3-methyl-4-[1-(4-tert-butylphenyl)3-methyl-5-oxo-2-pyrazolin-4-ylazo]-5-oxo-2-pyrazolin-1-yl}benzoic acid;

2-{3-methyl-4-[1-(3,4-dimethylphenyl)-3-methyl-5-oxo-2-pyrazolin-4-ylazo]-5-oxo-2-pyrazolin-1-yl}benzoic acid;

2-{3-methyl-4-[3-methyl-5-oxo-1-(3-trifluoromethylphenyl)-2-pyrazolin-4-ylazo]-5-oxo-2-pyrazolin-1-yl}acetic acid;

2-{3-methyl-4-[1-(3,4-dichlorophenyl)-3-methyl-5-oxo-1)-2-pyrazolin-4-ylazo]-5-oxo-2-pyrazolin-1-yl}acetic acid; and 2-{3-methyl-4-[1-(4-tert-butylphenyl)3-methyl-5-oxo-2-pyrazolin-4-ylazo]-5-oxo-2-pyrazolin-1-yl}acetic acid;

or a pharmaceutical acceptable salt, hydrate, solvate or ester thereof.

13. A process for preparing a pharmaceutical composition containing a pharmaceutically acceptable carrier or diluent and an effective amount of a compound of the Formula (I) as described in claim 1 and pharmaceutically acceptable salts, hydrates, solvates and esters thereof which process comprises bringing the compound of the Formula (I) into association with the pharmaceutically acceptable carrier or diluent.

14. A compound selected from:

4-{3-methyl-4-[1-(3,4-dimethylphenyl)-3-methyl-5-oxo-2-pyrazolin-4-ylazo]-5-oxo-2-pyrazolin-1-yl}benzoic acid;

4-{3-methyl-4-[3-methyl-5-oxo-1-(3-trifluoromethylphenyl)-2-pyrazolin-4-ylazo]-5-oxo-2-pyrazolin-1-yl}benzoic acid;

4-{3-methyl-4-[1-(4-iodophenyl)3-methyl-5-oxo-2-pyrazolin-4-ylazo]-5-oxo-2-pyrazolin-1-yl}benzoic acid;

4-{3-methyl-4-[1-(3,4-dichlorophenyl)-3-methyl-5-oxo-1)-2-pyrazolin-4-ylazo]-5-oxo-2-pyrazolin-1-yl}benzoic acid;

4-{3-methyl-4-[3-methyl-5-oxo-1-(quinolin-2-yl)-2-pyrazolin-4-ylazo]-5-oxo-2-pyrazolin-1-yl}benzoic acid;

4-{3-methyl-4-[1-(4-tert-butylphenyl)3-methyl-5-oxo-2-pyrazolin-4-ylazo]-5-oxo-2-pyrazolin-1-yl}benzoic acid;

3-{3-methyl-4-[1-(3,4-dimethylphenyl)-3-methyl-5-oxo-2-pyrazolin-4-ylazo]-5-oxo-2-pyrazolin-1-yl}benzoic acid;

3-{3-methyl-4-[3-methyl-5-oxo-1-(3-trifluoromethylphenyl)-2-pyrazolin-2-pyrazolin-4-ylazo]-5-oxo-2-pyrazolin-1-yl}benzoic acid;

3-{3-methyl-4-[1-(4-iodophenyl)3-methyl-5-oxo-2-pyrazolin-4-ylazo]-5-oxo-2-pyrazolin-1-yl}benzoic acid;

3-{3-methyl-4-[1-(3,4-dichlorophenyl)-3-methyl-5-oxo-1)-2-pyrazolin-4-ylazo]-5-oxo-2-pyrazolin-1-yl}benzoic acid;

3-{3-methyl-4-[3-methyl-5-oxo-1-(quinolin-2-yl)-2-pyrazolin-4-ylazo]-5-oxo-2-pyrazolin-1-yl}benzoic acid;

3-{3-methyl-4-[1-(4-tert-butylphenyl)3-methyl-5-oxo-2-pyrazolin-4-ylazo]-5-oxo-2-pyrazolin-1-yl}benzoic acid;

2-{3-methyl-4-[1-(3,4-dimethylphenyl)-3-methyl-5-oxo-2-pyrazolin-4-ylazo]-5-oxo-2-pyrazolin-1-yl}acetic acid;

2-{3-methyl-4-[3-methyl-5-oxo-1-(3-trifluoromethylphenyl)-2-pyrazolin-4-ylazo]-5-oxo-2-pyrazolin-1-yl}acid;

2-{3-methyl-4-[1-(3,4-dichlorophenyl)-3-methyl-5-oxo-1)-2-pyrazolin-4-ylazo]-5-oxo-2-pyrazolin-1-yl}acetic acid; and 2-{3-methyl-4-[-(4-tert-butylphenyl)3-methyl-5-oxo-2-pyrazolin-4-ylazo]-5-oxo-2-pyrazolin-1-yl}acetic acid;

or a pharmaceutical acceptable salt, hydrate, solvate or ester thereof.

* * * * *